United States Patent
Gadgil et al.

(10) Patent No.: US 12,285,366 B2
(45) Date of Patent: *Apr. 29, 2025

(54) SYSTEM AND METHOD FOR A THERMOREGULATED ENVIRONMENT

(71) Applicant: General Electric Company, Schenectady, NY (US)

(72) Inventors: Shruti Abhijit Gadgil, Bangalore (IN); Nagapriya Kavoori Sethumadhavan, Bangalore (IN)

(73) Assignee: General Electric Company, Schenectady, NY (US)

( * ) Notice: Subject to any disclaimer, the term of this patent is extended or adjusted under 35 U.S.C. 154(b) by 549 days.

This patent is subject to a terminal disclaimer.

(21) Appl. No.: 17/491,436

(22) Filed: Sep. 30, 2021

(65) Prior Publication Data

US 2022/0023129 A1    Jan. 27, 2022

Related U.S. Application Data

(63) Continuation of application No. 16/212,587, filed on Dec. 6, 2018, now Pat. No. 11,166,862.

(51) Int. Cl.
| | | |
|---|---|---|
| A61G 12/00 | (2006.01) | |
| A61B 5/00 | (2006.01) | |
| A61B 5/0205 | (2006.01) | |
| A61F 7/00 | (2006.01) | |
| A61G 10/02 | (2006.01) | |
| A61G 11/00 | (2006.01) | |

(Continued)

(52) U.S. Cl.
CPC .......... *A61G 12/00* (2013.01); *A61B 5/02055* (2013.01); *A61B 5/4836* (2013.01); *A61B 5/7246* (2013.01); *A61B 5/7267* (2013.01); *A61B 5/7275* (2013.01); *A61F 7/0053* (2013.01); *A61G 10/02* (2013.01); *A61G 11/00* (2013.01); *A61B 5/024* (2013.01); *A61B 5/0816* (2013.01); *A61B 5/4205* (2013.01); *A61B 2503/045* (2013.01); *A61F 2007/0086* (2013.01); *A61F 2007/0093* (2013.01); *A61G 2203/20* (2013.01)

(58) Field of Classification Search
None
See application file for complete search history.

(56) References Cited

U.S. PATENT DOCUMENTS 11,166,862 B2 * 11/2021 Gadgil .................. A61G 12/00

* cited by examiner

Primary Examiner — Christine H Matthews

(57) ABSTRACT

Various systems and devices are provided for determining a weaning readiness for weaning a patient from a thermoregulated microenvironment. In one example, a method includes receiving current patient parameters of the patient and applying a weaning model to the current patient parameters to calculate a weaning index representing a likelihood that the patient can be successfully weaned from the microenvironment. The method also includes outputting the weaning index for display on a display device or for storage in a medical record of the patient and upon outputting the weaning index, receiving one or more subsequent patient outcomes, the one or more subsequent patient outcomes comprising whether the patient developed any complications within the duration since being weaned from the microenvironment. The method also includes updating the weaning model based on the one or more received subsequent patient outcomes.

8 Claims, 7 Drawing Sheets

(51) Int. Cl.
*A61B 5/024* (2006.01)
*A61B 5/08* (2006.01)

SYSTEM AND METHOD FOR A THERMOREGULATED ENVIRONMENT

CROSS-REFERENCE TO RELATED APPLICATIONS

The present application is a continuation of and claims priority to U.S. patent application Ser. No. 16/212,587, filed Dec. 6, 2018, and titled "SYSTEM AND METHOD FOR A THERMOREGULATED ENVIRONMENT," which is incorporated by reference herein in its entirety.

FIELD

Embodiments of the subject matter disclosed herein relate to a thermoregulated microenvironment, and in particular to a weaning index for weaning a patient from a thermoregulated microenvironment.

BACKGROUND

Prematurely born infants require specialized treatment and care due to their small size and still-developing organs and physiological systems. Thus, premature infants are placed in devices that create a carefully controlled microenvironment around the infant. One type of device is generally referred to as an incubator in which the infant is placed within a physical enclosure and the temperature within the enclosure is carefully controlled with convective and/or radiant heating. Further, some microenvironments may include an oxygen enriched environment or humidity control.

BRIEF DESCRIPTION

In one embodiment, a method includes receiving a plurality of current patient parameters of a patient housed in a thermoregulated microenvironment, applying a weaning model to the plurality of current patient parameters to generate a weaning index representing a likelihood that the patient will be successfully weaned from the microenvironment if weaned at that time, the weaning model trained to correlate the current patient parameters with the likelihood based on historical data of prior patients and known outcomes for those prior patients, and outputting the weaning index for display on a display device and/or for storage in a medical record of the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of determining a readiness of patient to be weaned from a thermoregulated microenvironment. Currently, the determination of when a patient is ready to be weaned off the microenvironment varies widely among medical facilities. This determination may be based on the professional experience of the clinicians, availability of equipment, cost, and availability of skilled staff. Additionally, many medical facilities have no established guidelines for deciding when a patient can be weaned off the microenvironment, and even if medical facilities do have guidelines that dictate when a patient can be weaned, there is currently no consolidated single pathway/algorithm for weaning decision making that may be uniformly and broadly applied.

Thus, current approaches to determining when a patient should be weaned off the microenvironment may not sufficiently take into account the timing (e.g., patient status) that is most appropriate for the patient and that leads to the best outcome for the patient. Further, current approaches rely heavily on clinician judgement and do not typically include quantitative or objective measurements. Accordingly, non-patient driven factors (whether applied by the medical facility, the patient or guardian, or third parties such as insurance companies) may unduly influence the decision of when the patient should be weaned off the microenvironment, leading at least in some examples to patients being weaned earlier than may be ideal for successful patient outcomes, or in other examples, leading to patients being weaned later than necessary, thereby driving up costs, increasing risk of medical facility-acquired infections, and/or delaying parental bonding.

Thus, according to embodiments disclosed herein, artificial intelligence may be leveraged to analytically determine the weaning readiness of a patient. The weaning readiness may be represented by a weaning index. The weaning index may be determined using a combination of AI-driven data analytics and clinical workflow. The weaning index may be displayed to a clinician via a display device associated with microenvironment, via a mobile application executing on a clinician mobile device, and/or the weaning index may be stored as part of a patient medical record.

By relying on an analytically determined weaning index, the chance of early weaning (in resource-constrained medical facilities) may be reduced. Further, in some examples, particularly in medical facilities that are not necessarily resource-constrained, the weaning index may be trained to identify patient readiness for weaning in a manner that optimizes length of stay, such as reducing unnecessarily long patient stays in the microenvironment, which may decrease costs. The weaning index may utilize objective/quantitative evidence to support weaning decision making, which may help clinicians make decisions to optimize costs without jeopardizing patient health.

Figure 1:
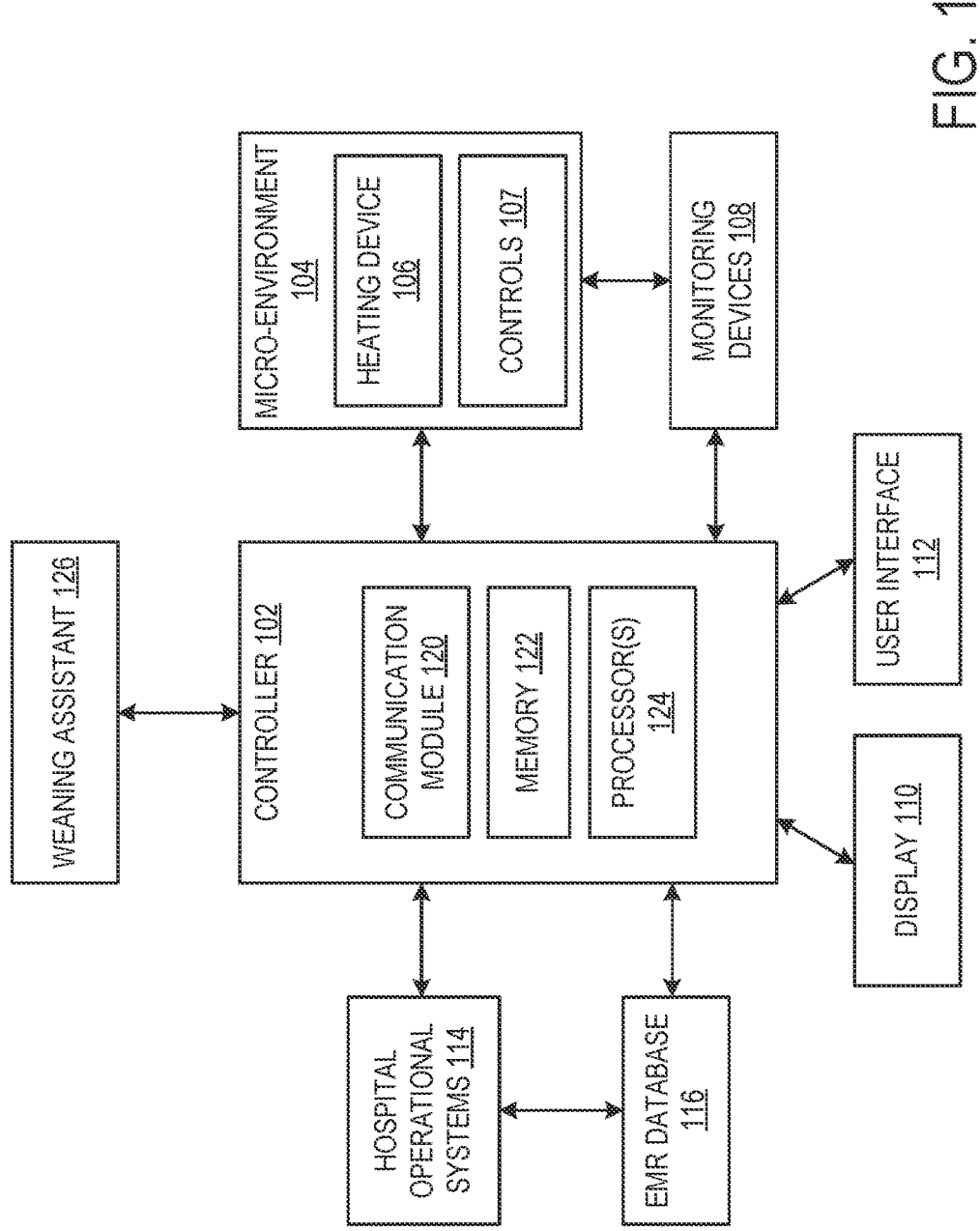
FIG. 1 schematically shows an example thermoregulated environment system.
Figure 2:
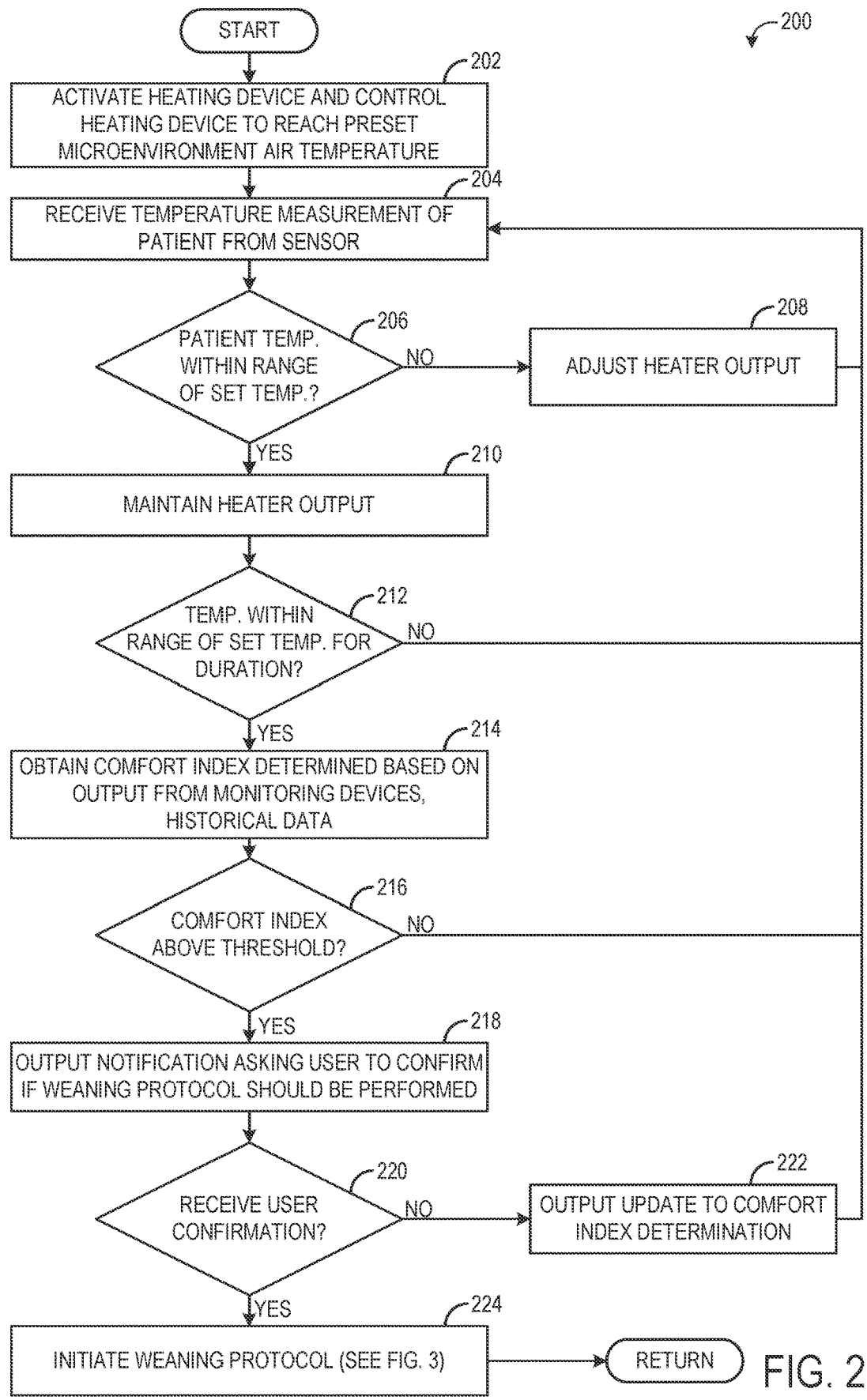
FIG. 2 is a flow chart illustrating a method for controlling a thermoregulated environment in a first mode.
Figure 5:
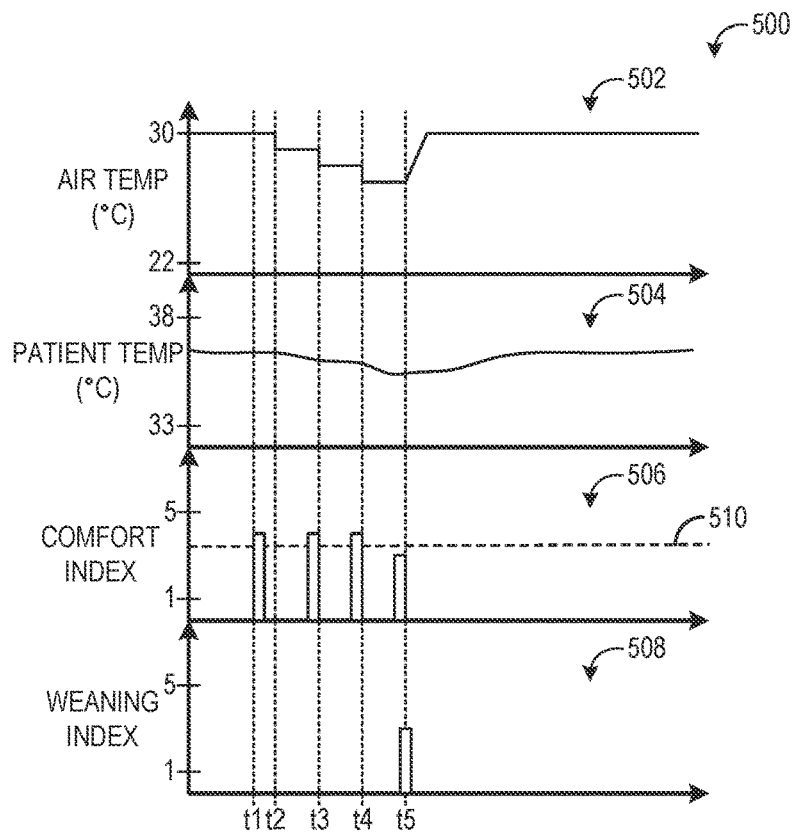
FIGS. 5 and 6 are example timelines showing parameters of interest for a patient during the execution of the methods of FIGS. 2 and 3.
Figure 6:
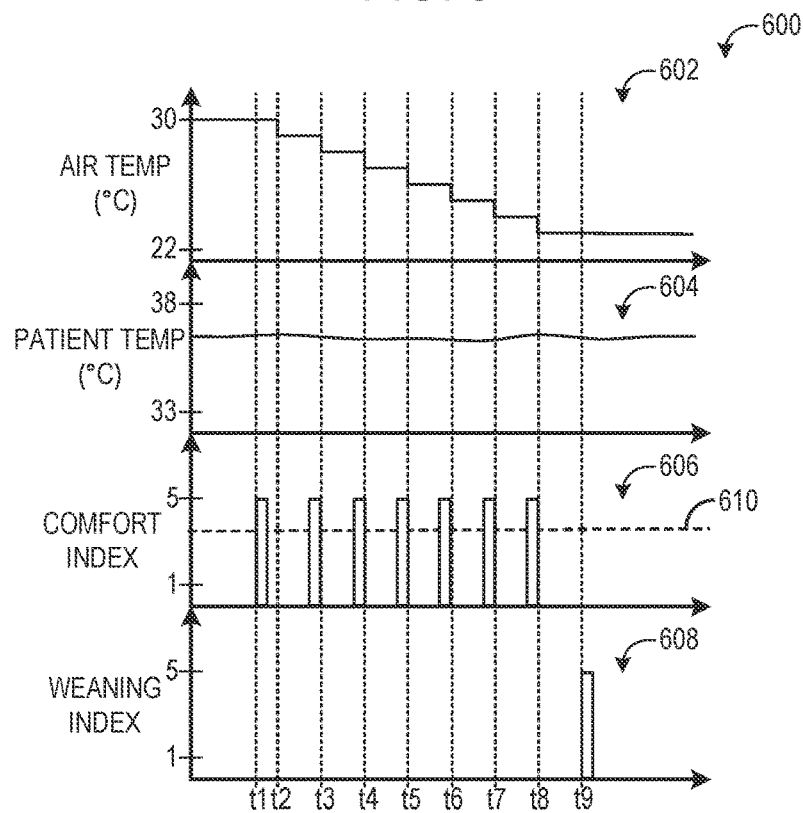

An example thermoregulated environment system is shown in FIG. 1. The thermoregulated environment system may include a heated microenvironment (e.g., incubator) configured to house a patient, such as a prematurely born infant, and at least regulate the air temperature surrounding the patient. The thermoregulated environment system may further include a controller configured to adjust the air temperature of the microenvironment based on a temperature of the patient, as shown in the method of FIG. 2. The controller may be further configured to, if the temperature of the patient has remained stable for a predetermined time period, execute a weaning protocol in order to determine the weaning readiness of the patient, as shown in method of FIG. 3. When the weaning protocol is executed, the controller may adjust the air temperature of the microenvironment to preset temperatures, and specifically to gradually reduce the air temperature of the microenvironment until the temperature reaches ambient temperature. Once the temperature reaches ambient temperature, and if patient health signs are stable, a weaning index is obtained and displayed to a user. The user may then consult the weaning index in order to determine if the patient should be weaned off the microenvironment. The weaning index may be calculated by a weaning assistant executed on the controller or a remote device, according to the method shown in FIG. 4. The weaning assistant may be an artificial intelligence based module that is trained (e.g., using machine learning) to calculate the weaning index based on patient parameters (e.g., vital signs) relative to historical data of prior patients. In one example, the weaning assistant may calculate the weaning index using a deep neural network, such as the deep neural network depicted in FIG. 7, that includes a large plurality of neurons or nodes, such as the neuron depicted in FIG. 8, arranged into layers. FIGS. 5 and 6 show example timelines of patient parameters during execution of the method of FIG. 3, for example.

FIG. 1 schematically shows an example thermoregulated environment system 100 that may be implemented in medical facility such as a hospital. Thermoregulated environment system 100 includes a microenvironment 104. Microenvironment 104 may be an incubator or other suitable device located within a patient's room, which may be a part of a neonatal intensive care unit (NICU) or other medical facility unit. Microenvironment 104 may include an enclosure which defines a microenvironment region, and may be mobile or stationary. Microenvironment 104 includes a heating device 106. Heating device 106 may be a convection-based heating device that includes a heating system that forces a flow of air through a heating element to heat the microenvironment around the patient. In other examples, heating device 106 may be a radiant-based heating device that includes a radiant heater canopy that includes heating elements, such as calrod heating elements, that direct radiant heat down on the patient in the microenvironment. In still further examples, heating device 106 may be a hybrid system that includes both convection-based heating elements and radiant-based heating elements. In this way, the temperature of the environment surrounding the patient in microenvironment 104 may be regulated (e.g., via feedback control from controller 102 and/or a controller of heating device 106) to maintain a consistent temperature appropriate for the needs of the patient. In some examples, microenvironment 104 may regulate other aspects of the environment surrounding the patient, such as oxygen content, humidity, etc. For example, microenvironment 104 may include a humidifier/de-humidifier or other component to regulate the humidity of the air in microenvironment 104.

System 100 further includes a variety of devices and features for monitoring and providing care to the patient in microenvironment 104, including monitoring devices 108. In some embodiments, monitoring devices 108 are completely disposed within the microenvironment region of the microenvironment. In other embodiments, a portion of the monitoring devices, such as physiological transducers, are disposed within the microenvironment, or otherwise extend into the microenvironment, and may be attached to the patient to acquire physiological signals from the patient. Non-limiting examples of monitoring devices 108 include an electrocardiograph (ECG) sensor, an electroencephalograph (EEG) sensor, a pulse oximetry (SpO2) sensor, a temperature sensor, a non-invasive blood pressure (NIBP) sensor, a humidity sensor, cameras, and other devices; however, it is understood that these are merely examples and many other types of patient monitoring devices may be used in the presently disclosed manner. In still further examples, monitoring devices 108 may include a connection to a remote service or services that may provide information of the ambient environment (e.g., of the medical facility and/or of the home at which the patient will reside once discharged from the medical facility), such as ambient temperature, ambient humidity, and particulate matter level. Monitoring devices 108 may be coupled to controller 102, which may output representations of the signals from the monitoring devices on a display 110. Display 110 may be similarly located fully or partially within the microenvironment region. In an alternative embodiment, the display 110 is located outside of the microenvironment region. Display 110 is operated to visually present the acquired physiological information to a clinician.

Microenvironment 104 further includes microenvironment controls 107. These microenvironment controls 107 include the mechanical and electronic components and controls of systems of the microenvironment for maintaining desirable levels of temperature, humidity, and oxygen within the microenvironment. These controls include controls to regulate the radiant heater and/or the convective heater described above. For example, an amount of current supplied to a heating element of the heating device may be controlled to maintain the microenvironment at a set temperature and/or to maintain patient temperature at a set temperature. Further, the microenvironment controls 107 may include actuator(s) that may be adjusted to control microenvironment oxygen content, humidity, and so forth.

Thermoregulated environment system 100 includes a controller 102. Controller includes a communication module 120, memory 122, and processor(s) 124. Controller 102 is operatively coupled to display 110 and a user interface 112. User interface 112 may include a graphical user interface presented on a touch screen, such as display 110, and/or user-actuated devices such as a mouse, keyboard, buttons, switches, etc. User input sent to/received by controller 102 may be entered via user interface 112.

Controller 102 may be communicatively coupled to hospital operational systems 114. Hospital operational systems 114 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, hospital operational systems 114 and/or controller 102 may be communicatively coupled to an electronic medical records (EMR) database 116. EMR database 116 may be an external database accessible by controller 102 via a secured hospital interface, or EMR database 116 may be a local database (e.g., housed on a device of the hospital). EMR database 116 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, preexisting medical conditions, current medications, allergies, surgical history, past medical screenings and procedures, past hospitalizations and visits, etc.

As explained above, microenvironment 104 may be adapted (e.g., sized) to house an infant, such as a prematurely born infant, and may provide a heated environment and, in some examples, regulated air (e.g., air that has been filtered to be free of air-borne pathogens and/or regulated to a specific oxygen content, humidity, etc.) to the infant to provide a controlled environment via which the infant may be sheltered from ambient conditions that may deter infant growth and development. Once the infant has reached a particular stage of development (e.g., equivalent to a non-prematurely born infant), a clinician may desire to wean the infant from the microenvironment so the infant may be sent to another clinical setting (e.g., in a room with the infant's mother) or sent home. Generally, whether an infant is ready to be weaned from the microenvironment is a subjective determination that may vary from hospital to hospital and even from clinician to clinician. Further, cultural or economic factors may influence clinicians to wean infants earlier than may be preferable to avoid subsequent issues and/or readmittance to the hospital. For example, each medical facility (such as hospital or neonatal unit) may have its own guidelines for how to determine if an infant is ready to be weaned from the microenvironment, but these guidelines may be inconsistent across medical facilities, leave much of the decision making up to the clinician, and may not be evidence-based. Further still, once an infant is deemed ready to be weaned, many medical facilities institute a trial and error approach, where the infant is removed from the microenvironment and monitored for a few hours, and then moved back to the microenvironment if the infant's vital signs indicate that the infant is not ready to be removed from the microenvironment. This approach may be resource intensive and may expose the infant to undue risk that may impact the infant's outcome.

Thus, system 100 may include a weaning assistant 126 to provide a stream-lined, consistent, and evidence-based predication of whether a patient is ready to be weaned from a microenvironment. Weaning assistant 126 may be an artificial intelligence-based module that may be stored and/or executed on a suitable device or devices. As shown, weaning assistant 126 is stored on a device that is remote from controller 102, such as a central server that is in wired or wireless communication with controller 102. Weaning assistant 126 is trained to predict the likelihood that a patient can be successfully weaned from the microenvironment, where "successfully" weaned refers to the patient being weaned and not being readmitted to the microenvironment at a later time and/or the patient being discharged from the medical environment without being readmitted to the medical environment within a threshold amount of time. The prediction is output in the form of the weaning index, which may be a numerical value in a range of a relatively low value (e.g., 1) indicating the patient is not ready to be weaned to a relatively high value (e.g., 5) indicating the patient is ready to be weaned. The weaning index may be displayed to a user (e.g., via display 110) to assist the user in deciding if the patient housed in microenvironment 104 should be weaned (e.g., removed) from the microenvironment.

The weaning index may be calculated by weaning assistant 126 based on information received from monitoring devices 108 (e.g., heart rate, respiration rate, body temperature, current length of stay in the microenvironment), user input data, and/or historical data. The user input data may include user-monitored parameters of the patient, such as sucking reflex/acceptance of oral feeds, urination frequency, gestational age of the patient, and/or the number of days since the birth of the patient. The historical data may include the above-described patient parameters (e.g., heart rate, respiration rate, body temperature, sucking reflex, length of stay in the microenvironment, as well as patient age and gestational age at which the patient was born) for each of a plurality of other patients previously housed in a thermo-regulated microenvironment, along with known outcomes for each of the patients (such as readmittance rate and other outcomes). For example, weaning assistant 126 may be trained using the historical data described above. Then, for a particular patient that may ready to be weaned, weaning assistant 126 may calculate a weaning index based on the measured/determined parameters for that patient relative to the historical data.

While the weaning index may provide a robust prediction of a patient's likelihood of being successfully weaned from a microenvironment, the rapid change in environment from the microenvironment to the ambient environment may still pose risks, particularly to patients whose weaning indexes are intermediate values in the range of values described above (e.g., a weaning index of 3 or 4). Thus, in some examples, the weaning index may be calculated after the microenvironment has slowly transitioned from being highly regulated to being unregulated. For example, the weaning index may be calculated once the microenvironment has transitioned from a preset, non-ambient temperature to ambient temperature and/or once the microenvironment has transitioned from a preset, non-ambient humidity to ambient humidity. The transition may be relatively slow (e.g., 0.5° C. per hour) and each time the temperature and/or humidity of the microenvironment is changed, a comfort index may be calculated and displayed to a user. The comfort index may indicate how well the patient is tolerating the change in temperature or other parameters. If the comfort index indicates the patient is tolerating the change in temperature, the temperature change may be continued until the microenvironment reaches ambient temperature, at which point the weaning index may be determined. The comfort index may be calculated by weaning assistant 126 in a manner similar to the weaning index, but to calculate the comfort index, weaning assistant 126 may be trained with different outcomes than the weaning index. For example, the historical patient parameters input to weaning assistant 126 may be the same for both the comfort index and the weaning index, but the outcomes associated with the historical patient parameters may be different. As explained above, weaning assistant 126 may be trained to calculate the weaning index using microenvironment, NICU, and hospital readmittance rates as known outcomes, while weaning assistant 126 may be trained to calculate the comfort index using duration of stable vital signs as known outcomes (e.g., for a given set of patient parameters that includes the air temperature of the microenvironment at the time the patient parameters were collected, the known outcome may include whether the patient parameters remained stable for a predetermined amount of time at the air temperature).

Once the weaning index is determined, the weaning index may be displayed to a user (e.g., a clinician such as a doctor or nurse), such as via display 110, and the weaning index may be saved in the patient's medical record (e.g., stored in EMR database 116). The user may then decide whether to remove the patient from the microenvironment based on the weaning index. For example, if the weaning index is high (e.g., 4 or 5), the user may decide to remove the patient from the microenvironment. If the weaning index is low, the user may decide to leave the patient in the microenvironment. In contrast, the comfort index may not be displayed to a user and may only be used to determine if the temperature of the microenvironment should be adjusted and/or if the patient is nearing weaning and thus a weaning index should be calculated.

The weaning index may be incorporated into clinician or medical facility guidelines for determining when to remove a patient from a microenvironment. For example, a medical facility may determine that a patient is to be removed from the microenvironment when the patient's weaning index has a value of 4 or 5, and the medical facility may dictate various different monitoring or discharge procedures based on the specific weaning index. For example, if a patient's weaning index has a value of 5, the guidelines may dictate that the patient be discharged from the medical facility unit (e.g., NICU) upon removal from the microenvironment. If the patient's weaning index has a value of 4, the guidelines may dictate that the patient be removed from the microenvironment, but be maintained in the medical facility unit for an additional 24 hours for monitoring. Likewise, if the patient's weaning index has a value of 3 or lower, the guidelines may dictate that the patient be maintained in the microenvironment with the heating device of the microenvironment in a feedback mode (where the output of the heating device is adjusted based on the patient's temperature), but the guidelines may dictate different actions beyond maintaining the patient in the microenvironment based on the weaning index value. For example, if the weaning index has a value of 3, the weaning index may be calculated again in 24 hours, while if the weaning index has a value of 2, the weaning index may be calculated again in 48 hours. If the weaning index has a value of 1, the guidelines may dictate that additional monitoring or treatment be provided to the patient, for example. In still further examples, additionally or alternatively, the weaning index may be stored in a patient's medical record or other patient-related documents or records, so that the weaning index may be accessed during patient/family counseling of treatment decisions for the patient (such as discharge or continuation of treatment decisions) and/or made available as evidence during medicolegal proceedings.

Weaning assistant 126 may be implemented in a non-transitory memory and may be executable by one or more processors of a computing system, such as a central server in communication with controller 102 and/or other computing devices, such as clinician devices and/or hospital operational systems 114. In some embodiments, weaning assistant 126 may be fully or partially implemented on controller 102, or a device that is included as part of the hospital operational systems 114. In some embodiments, weaning assistant 126 may be implemented in a cloud in communication with the controller 102. In some embodiments, portions of weaning assistant 126 are implemented on different devices, such as any appropriate combination of the controller 102, a care provider device, the cloud, etc.

Weaning assistant 126 may be trained to calculate a weaning index, and in some examples, to calculate a comfort index, using machine learning (e.g., deep learning), such as random forest, neural networking, or other training mechanisms. For example, weaning assistant 126 may be trained using measured/monitored parameters of a plurality of patients as well as the outcome(s) of each patient. The measured/monitored parameters may include heart rate, respiration rate, temperature, weight/weight gain, acceptance of oral feeds, sucking reflex, gestational age at time of weaning, and duration of time in the microenvironment at the time the patient was weaned off a microenvironment (or within a given time duration of the patient being weaned off the microenvironment, such as within 24 hours before being weaned). The same measured/monitored parameters may be used to train weaning assistant 126 to calculate the comfort index; however, the measured/monitored parameters used to train for determining the comfort index may be obtained at any time over the course of the patient's stay in the NICU and/or microenvironment, and may be tagged with the microenvironment or ambient temperature at the time the parameters were obtained, for example.

The outcomes for training weaning assistant 126 to calculate a weaning index may include whether the patient was readmitted to the microenvironment, whether the patient was readmitted to the medical facility within a threshold amount of time of being discharged from the medical facility, other outcomes related to the initial diagnosis of the patient (e.g., why the patient was placed in the microenvironment to begin with), such as complications related to the patient being born prematurely, and/or ambient conditions at the time the patient was weaned (whether in the medical facility or in the patient's home). The outcomes for training weaning assistant 126 to calculate a comfort index may include the ability of the patient to maintain a given set of parameters for a predetermined duration (e.g., an hour, 24 hours) at a given air temperature/humidity, how long the patient was monitored at the given set of parameters at the given air temperature/humidity (e.g., how long the patient remained stable), how much the given parameters changed upon a change in air temperature/humidity, and so forth. The weaning assistant 126 may thus be trained, based on the training patient parameters and associated known outcomes, to predict the likelihood that any set of patient parameters will result in a positive outcome for both the comfort index (e.g., stable parameters upon a change in microenvironment temperature/humidity) and the weaning index (e.g., no complications and no readmittance). The predicted likelihood may be expressed as a value on a scale, as described above, or other suitable form, such as a binary ready/not ready for weaning for the weaning index and stable/unstable signs for the comfort index.

Further, weaning assistant 126 may be configured to learn the above-described weaning index and comfort index calculations in a clinician and/or medical facility specific manner, and may be configured to continue to learn and update the weaning index and comfort index calculations as weaning assistant 126 receives input from clinicians. For example, weaning assistant 126 may be trained that medium to low patient weight (e.g., compared to a standard weight curve by age) may be indicative of a low likelihood of successful weaning, but then may be trained for a specific medical facility that low patient weight is common amongst the population served by the medical facility and thus may have less relevance. As another example, if a high (e.g., 4 or 5) weaning index is calculated for a given patient and presented to a clinician, and the clinician opts not to wean the patient at that time, weaning assistant 126 may update the weaning index determination (e.g., such that some or all of the parameters that led to the high weaning index may be given less weight in future weaning index determinations). The updated weaning index determination may be updated for all medical facilities and all clinicians, or the update may be made in a more targeted manner (e.g., only for that clinician or that medical facility). In still further examples, once a patient is weaned, subsequent outcomes for the patient may be tracked and sent to weaning assistant 126. The subsequent outcomes may include whether the patient was readmitted to the medical facility and/or microenvironment, weight gain following weaning, ambient conditions in the patient's home, and so forth. Weaning assistant 126 may learn from the subsequent outcomes and adjust future weaning index determinations accordingly. For example, if a weaning index for a patient is high enough to warrant weaning, but then the patient is readmitted to the microenvironment 24 hours later, the weighting/connection of the parameters used to determine the original weaning index may be adjusted.

Controller 102 includes a communication module 120, memory 122, and processor(s) 124 to send and receive communications, generate and output graphical user interfaces, send and receive medical data, send controls to microenvironment, and other tasks. Further, in some examples, controller 102 may store and execute at least portions of weaning assistant 126 and/or may send and receive information to/from weaning assistant 126, such sending as patient monitoring information (e.g., from monitoring devices 108 and/or EMR database 116) and user input data to weaning assistant 126 and/or receiving a calculated weaning index and/or comfort index from weaning assistant 126.

Communication module 120 facilitates transmission of electronic data within and/or among one or more systems. Communication via communication module 120 can be implemented using one or more protocols. In some examples, communication via communication module 120 occurs according to one or more standards (e.g., Digital Imaging and Communications in Medicine (DICOM), Health Level Seven (HL7), ANSI X12N, etc.). Communication module 120 can be a wired interface (e.g., a data bus, a Universal Serial Bus (USB) connection, etc.) and/or a wireless interface (e.g., radio frequency, infrared, near field communication (NFC), etc.). For example, communication module 120 may communicate via wired local area network (LAN), wireless LAN, wide area network (WAN), etc. using any past, present, or future communication protocol (e.g., BLUETOOTH™, USB 2.0, USB 3.0, etc.).

Memory 122 one or more data storage structures, such as optical memory devices, magnetic memory devices, or solid-state memory devices, for storing programs and routines executed by processor(s) 124 to carry out various functionalities disclosed herein. Memory 122 may include any desired type of volatile and/or non-volatile memory such as, for example, static random access memory (SRAM), dynamic random access memory (DRAM), flash memory, read-only memory (ROM), etc. Processor(s) 124 may be any suitable processor, processing unit, or microprocessor, for example. Processor(s) 124 may be a multiprocessor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

While not specifically shown in FIG. 1, additional devices described herein (devices associated with hospital operational systems 114, clinician devices, etc.) may likewise include user input devices, memory, processors, and communication modules/interfaces similar to communication module 120, memory 122, and processor(s) 124 described above, and thus the description of communication module 120, memory 122, and processor(s) 124 likewise applies to the other devices described herein.

FIG. 2 is a flow chart illustrating a method 200 for a thermoregulated environment system located in a medical facility, such as a hospital. Method 200 may be executed by a processor of a computing device operatively coupled to a microenvironment (such processor(s) 124 of controller 102 of FIG. 1) according to instructions stored on a non-transitory memory of the device (e.g., memory 122 shown in FIG. 1) in combination with the various signals received at the computing device from components of the thermoregulated environment system (e.g., patient medical data signals and/or environment signals from monitoring devices 108, communication from hospital operational systems 114, communication from weaning assistant 126, etc.) and signals sent from the controller to microenvironment controls 107, a display device (e.g., display 110), clinician devices, and/or other system components.

At 202, a heating device of a microenvironment is activated, and the heating device is controlled to reach a preset microenvironment air temperature. The heating device, such as heating device 106 of microenvironment 104 of FIG. 1, may be activated upon a user input being received requesting activation of the heating device. The heating device may be activated before a patient is placed into the microenvironment, in order to pre-warm the microenvironment to a temperature above ambient temperature. The preset microenvironment air temperature may be input by a user, or the preset temperature may be a default temperature. Further, in some examples, the air in the microenvironment may be further pre-conditioned before a patient is placed in the microenvironment, such as by adjusting the oxygen content of the air, the humidity of the air, etc. Once the microenvironment is conditioned to the preset temperature, the patient may be placed in the microenvironment.

At 204, a temperature measurement of the patient is received from a temperature sensor configured to measure a temperature of the patient in the microenvironment. The temperature sensor may be one of the monitoring devices 108 of FIG. 1. At 206, method 200 determines if the measured patient temperature is within range of a set patient temperature. The set patient temperature may be input by a user, or the set patient temperature may be a default or otherwise predetermined temperature that is based on the location of the temperature sensor on the patient, such as skin temperature (e.g., 36.5° C.). In one example, the measured patient temperature may be determined to be in range of the set patient temperature when the measured patient temperature is within 0.3° C. of the set patient temperature (e.g., if the set patient temperature is skin temperature, the range may be 36.2-36.8° C.), or other suitable temperature range. In some examples, a humidity measurement of the air in the microenvironment may be received from a humidity sensor, and the method may determine if the measured humidity is within range (e.g., within 5-10%) of a preset humidity.

If the measured patient temperature is not within range of the preset patient temperature, method 200 proceeds to 208 to adjust the output of the heating device. For example, an amount of current or voltage supplied to the heating element(s) of the heating device may be adjusted (e.g., increased), a rate of airflow in the microenvironment may be adjusted, or other suitable adjustment may be made to increase or decrease the amount of heat directed to the patient. The amount the heater output is adjusted may be based on an error between the measured patient temperature and set patient temperature and using a suitable control scheme, such as a PID controller. Upon adjusting the heater output (and once sufficient time has passed for the air temperature of the microenvironment to change and for the patient to respond to the changed air temperature), method 200 proceeds back to 204 to again receive measured patient temperature. In some examples, if the measured humidity is not within range of the preset humidity, the humidity of the air may be adjusted by controller a humidifier or dehumidifier.

Returning to 206, if the measured patient temperature is within range of the set patient temperature, method 200 proceeds to 210 to maintain heater output at the current output. (Likewise, if humidity is within range of the preset humidity, the method may maintain current humidifier/dehumidifier output.) At 212, method 200 determines if the measured patient temperature has been within range of the set patient temperature for a predetermined duration, such as 24 hours. If the measured patient temperature has not been within range of the set patient temperature for the duration, method 200 loops back to 204 to continue to monitor patient temperature. If the measured patient temperature has been within range of the set patient temperature for at least the duration, method 200 proceeds to 214 to obtain a comfort index of the patient that is determined based on output from the monitoring devices and historical data. The comfort index may provide a distillation of current patient status (e.g., positive, negative, trending upward, trending downward) that may be used to determine if the patient is stable enough to proceed towards weaning. For example, as explained above with respect to FIG. 1, the comfort index may be determined by an AI-based module, such as weaning assistant 126, that is trained to output the comfort index based on current and previous patient parameters measured by the various monitoring devices and/or input by a user (such as weight, respiration rate, heart rate, etc.), where the AI-based module is trained using similar parameters of prior (other) patients measured while the patients were housed in a microenvironment, and known outcomes for each patient (e.g., whether the patient remained stable for a predetermined amount of time after a change in air temperature, how long the patient remained in the microenvironment, if the patient developed any complications, etc.).

At 216, method 200 determines if the comfort index is above a threshold. The threshold comfort index may be a suitable threshold that indicates the patient has a high likelihood of remaining stable, that indicates the patient's vital signs/health indicators are trending upward (e.g., toward normal ranges for newborn infants) rather than downward, or other positive indication. For example, if the comfort index is a value on a scale of 1-5 with 1 meaning unstable vital signs and a high likelihood of poor tolerance of any changes to the microenvironment and 5 meaning stable vital signs and a low likelihood of poor tolerance of changes to the microenvironment, the threshold may be a comfort index value of 3 or 4.

If the comfort index is not above the threshold, method 200 proceeds back to 204 to continue to perform temperature feedback-based control of the heating device to maintain the temperature of the patient at the set patient temperature (and in some examples, also perform feedback-based control of microenvironment humidity). If the comfort index is above the threshold, method 200 proceeds to 218 to output a notification asking a user (such as a clinician) to confirm if a weaning protocol should be performed. Based on the patient temperature being maintained at the set temperature for the duration, and based on the comfort index being above the threshold, the patient may be ready to be weaned from the microenvironment. Before weaning the patient from the microenvironment, a weaning index may be obtained that predicts the likelihood that the patient will be successfully weaned from the microenvironment. Further, before weaning, the temperature and/or humidity of the microenvironment may be gradually adjusted to ambient temperature/humidity, which may reduce the likelihood of negative outcomes relative to simply removing the patient from the microenvironment, should the patient be unable to tolerate a lowered microenvironment temperature. The weaning index and gradual lowering of the temperature of the microenvironment may be obtained/instituted during the weaning protocol, which is performed in anticipation of weaning the patient. However, the user may not desire to wean the patient at this time, due to other outstanding factors known by the user but not reflected in the comfort index, for example. Thus, the clinician is given the opportunity to decide whether the weaning protocol should be performed.

At 220, method 200 determines if a user confirmation of the weaning protocol has been received. If user confirmation of the weaning protocol is not received (for example, if the user enters an input indicating that the weaning protocol should not be performed at this time and/or if the gestational age is less than 32 weeks and/or the days from birth is less than seven days, for example), method 200 proceeds to 222 to output an update to the comfort index determination. For example, one or more of the factors used to determine the comfort index may be given a lower weight, or the outcome associated with the factors used to determine the comfort index may be changed (e.g., from more likely to be weaned to less likely to be weaned). The update to the comfort index may be output to a weaning assistant module executing on the computing device (e.g., controller 102), or the update may be sent to a remote device executing a weaning assistant module, such as central server in communication with the computing device. In this way, the comfort index determination may continue to be updated based on user input and current patient parameters, which may cause the comfort indexes calculated in the future to be more accurate, at least with respect to the current user or medical facility. Method 200 then returns to 204 to continue performing the temperature feedback control of the microenvironment.

If user confirmation is received at 220, method 200 proceeds to 224 to initiate the weaning protocol, which will be described in more detail below with respect to FIG. 3. Briefly, as explained above, the weaning protocol may be performed in anticipation of weaning the patient, and may include a gradual lowering of the microenvironment air temperature to ambient temperature. Each time the temperature is lowered, the comfort index may be calculated to ensure that the patient is tolerating the change in temperature. Once ambient temperature is reached, a weaning index is calculated that represents the likelihood the patient will be successfully weaned from the microenvironment. If the weaning index indicates the patient has a high likelihood of being successfully weaned, the user may choose to wean the patient, while if the weaning index indicates the patient has a low likelihood of being successfully weaned, the user may choose to maintain the patient in the microenvironment.

Figure 3:
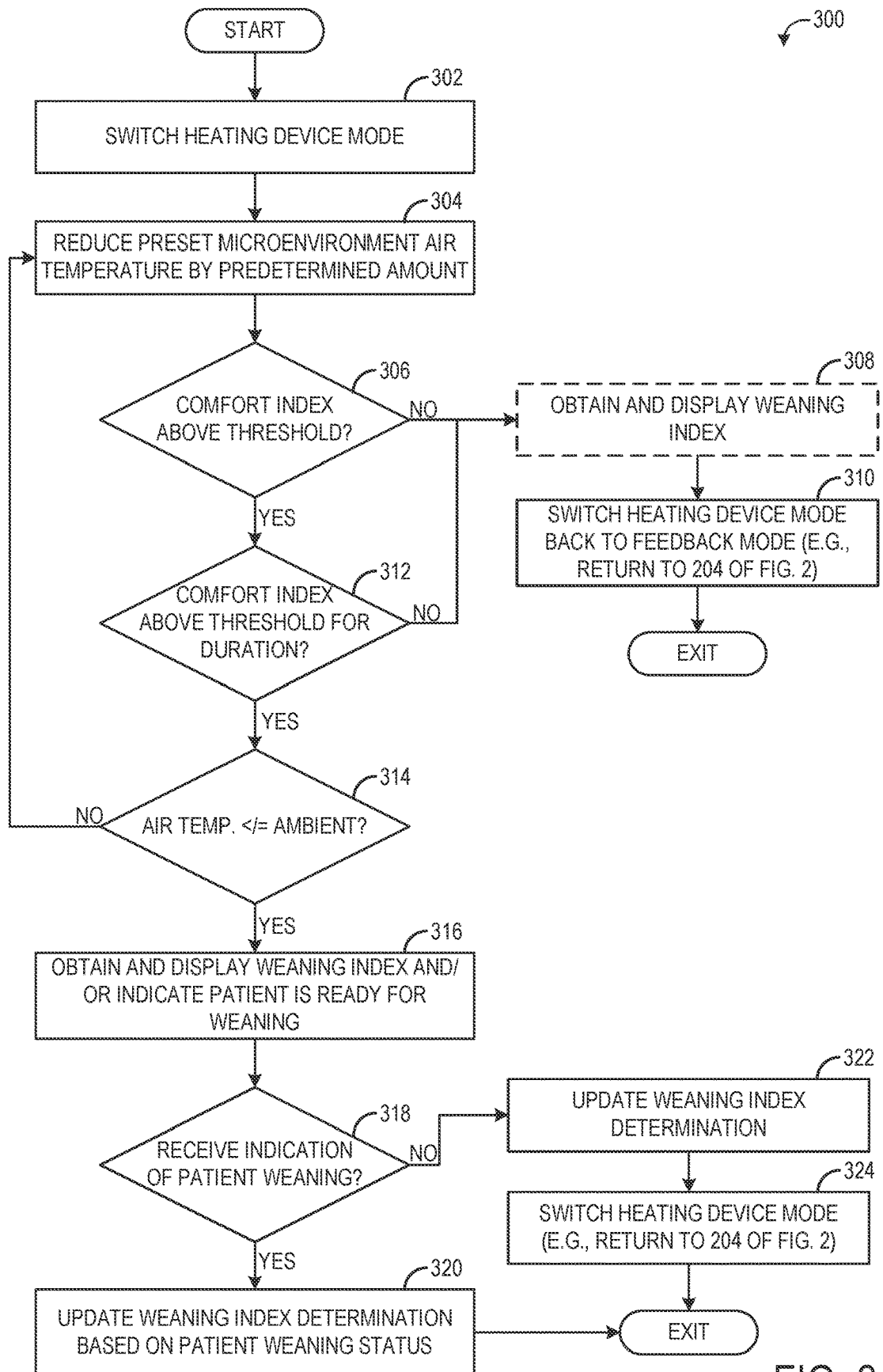
FIG. 3 is a flow chart illustrating a method for executing a weaning protocol, including controlling a thermoregulated environment in a second mode.

FIG. 3 illustrates a method 300 for performing a weaning protocol in a thermoregulated environment system located in a medical facility, such as a hospital. Method 300 may be executed by a processor of a computing device operatively coupled to a microenvironment (such processor(s) 124 of controller 102 of FIG. 1) according to instructions stored on a non-transitory memory of the device (e.g., memory 122 shown in FIG. 1) in combination with the various signals received at the computing device from components of the thermoregulated environment system (e.g., patient medical data signals and/or environment signals from monitoring devices 108, communication from hospital operational systems 114, etc.) and signals sent from the controller to a display device (e.g., display 110), a weaning assistant (e.g., weaning assistant 126), clinician devices, and/or other system components. In some examples, method 300 may be performed as part of method 200, e.g., in response to a user confirmation to perform the weaning protocol upon the patient temperature being maintained at the set temperature and the comfort index being above the threshold. In other examples, method 300 may be executed in response to a request from a user or under other conditions.

At 302, method 300 switches the heating device mode. The heating device of the microenvironment may normally operate in a feedback mode, where the output of the heating device is controlled based on measured patient temperature, in order to maintain the patient temperature at a set patient temperature. During the weaning protocol, the heating device may be switched to operate in a weaning mode, where the heating device is not controlled based on measured patient temperature but is instead controlled to gradually lower the microenvironment air temperature until ambient temperature is reached.

At 304, the preset microenvironment air temperature is reduced by a predetermined amount, such as 0.5° C. Additionally, in some examples, the preset microenvironment humidity may be adjusted by a predetermined amount, such as decreasing the humidity toward ambient humidity. The amount the humidity is adjusted may be based on the difference between microenvironment humidity and current ambient humidity, and in some examples may be a set percentage of the difference (e.g., the humidity may be adjusted by an amount equivalent to 25% of the difference). At 306, method 300 determines if the patient's comfort index is above the threshold. The comfort index for the patient may be obtained once the microenvironment air temperature has been lowered to the reduced air temperature, using the most recently available patient parameters (e.g., heart rate, respiration rate, temperature, etc.). The threshold may be the same threshold described above with respect to FIG. 2. As an example, if the microenvironment air temperature is reduced and the patient is unable to maintain proper body temperature, the patient may begin to increase oxygen usage, which may result in an increased respiration rate, leading to a reduced comfort index.

If the comfort index is not above the threshold, method 300 proceeds to 308 to optionally obtain and display the weaning index for the patient. The weaning index may be determined by a weaning assistant executing on the computing device and/or a remote device, such as a central server. The weaning index may indicate the probability the patient could be successfully weaned, based on the current patient parameters determined by the monitoring devices (e.g., heart rate, respiration rate, temperature), determined from user input (e.g., sucking reflex), and/or obtained from the patient EMR (e.g., weight, duration of stay in the microenvironment, date of birth relative to due date (also referred to as gestational age), number of days since birth). The weaning assistant may be trained to compute a weaning index value based on the current patient parameters relative to historic data of other patients (e.g., the same parameters obtained/measured for the current patient, but from other patients) and known outcomes for those patients. While the low comfort index indicates that the patient is likely not ready for weaning, the weaning index may still be displayed in order to provide the user with additional understanding of the patient state. Further, while not shown in FIG. 3, the weaning index may be saved in the patient's medical record. At 310, the heating device mode is switched back to the feedback mode and at least in some examples, the method may return back to 204 of FIG. 2.

Returning to 306, if the comfort index is above the threshold, method 300 proceeds to 312 to determine if the comfort index has remained above the threshold for a predetermined duration, such as an hour since the microenvironment temperature was reduced. For example, the comfort index may be re-determined an hour after the temperature of the microenvironment is reduced, or the comfort index may be re-determined periodically over the course of the predetermined duration (e.g., once every 15 minutes). If the comfort index did not remain above the threshold for the predetermined duration, for example if the comfort index dropped to or below the threshold within the predetermined duration, the method proceeds to optionally obtain and display the weaning index and switch the heating device mode. If the comfort index has remained above the threshold for the predetermined duration, for example if the comfort index was above the threshold each time the comfort index was calculated over the predetermined duration, method 300 proceeds to 314 to determine if the current microenvironment air temperature is equal to or below ambient temperature. If not, for example if the microenvironment air temperature is still above ambient temperature, method 300 loops back to 304 to again reduce the microenvironment air temperature by the predetermined amount and then monitor the patient comfort index. In some examples, similar to the microenvironment air temperature, the microenvironment humidity may be adjusted toward ambient humidity each time the comfort index stays above the threshold for the duration.

If the microenvironment air temperature is equal to or less than current ambient temperature, method 300 proceeds to 316 to obtain and display the weaning index for the patient and/or indicate that the patient is ready for weaning. The weaning index is obtained from an AI-based weaning assistant, as explained above. The weaning index obtained at 316 may be the most recent weaning index for the patient and may be computed based on the most recently-available patient parameters, e.g., most recent heart rate, respiration rate, and/or historical data, etc. The weaning index may be displayed on a suitable device, such as display 110 coupled to controller 102, or on a display of a clinician computing device. Further, the obtained weaning index may be saved in the patient's medical record (e.g., sent to EMR database 116). In some examples, method 300 may compare the weaning index to a threshold and determine if the patient is ready for weaning based on the weaning index being above the threshold. If the patient is ready for weaning, the method may include outputting a notification for display indicating that the patient is ready for weaning. However, if the weaning index is not above the threshold, the method may include outputting a notification indicating that the patient may not be ready for weaning.

At 318, method 300 determines if an indication of patient weaning has been received. For example, upon displaying the weaning index, a notification may also be output for display asking the user to confirm if the user is initiating weaning, and thus receiving an indication that the patient is being weaned may include receiving a user input confirming that the patient is being weaned. In other examples, the indication may be based on the state of the microenvironment, e.g., whether the microenvironment is turned off or turned back to the feedback mode. If an indication is received that the patient is being weaned, method 300 proceeds to 320 to update the weaning determination based on the patient weaning status. For example, a notification may be sent to the weaning assistant that the patient is being weaned, and the weaning assistant may learn that the weaning index is high enough to warrant weaning. The weaning assistant may then re-weight the patient parameters, such that those parameters are given a higher weight (which may result in a higher weaning index value being selected for those same parameters in the future). Method 300 then ends.

If an indication of patient weaning is not received, method 300 proceeds to 322 to update the weaning index determination. For example, if the weaning index is relatively high (e.g., 4), but the patient is not weaned, a notification may be sent to the weaning assistant, and the weaning assistant may learn that the attending clinician (or medical facility) prefers not to wean patients at that weaning index. Further, the weaning assistant may re-tune the algorithm used to compute the weaning index/re-weight the patient parameters, such that those parameters are given a lower weight (which may result in a lower weaning index value being selected for those same parameters in the future). If the heating device mode has not already been switched, the heating device mode may be switched back to the feedback mode at 324, and the method may return to 204 of method 200 to continue carrying out the feedback based control and eventually re-evaluate for weaning.

Figure 4:
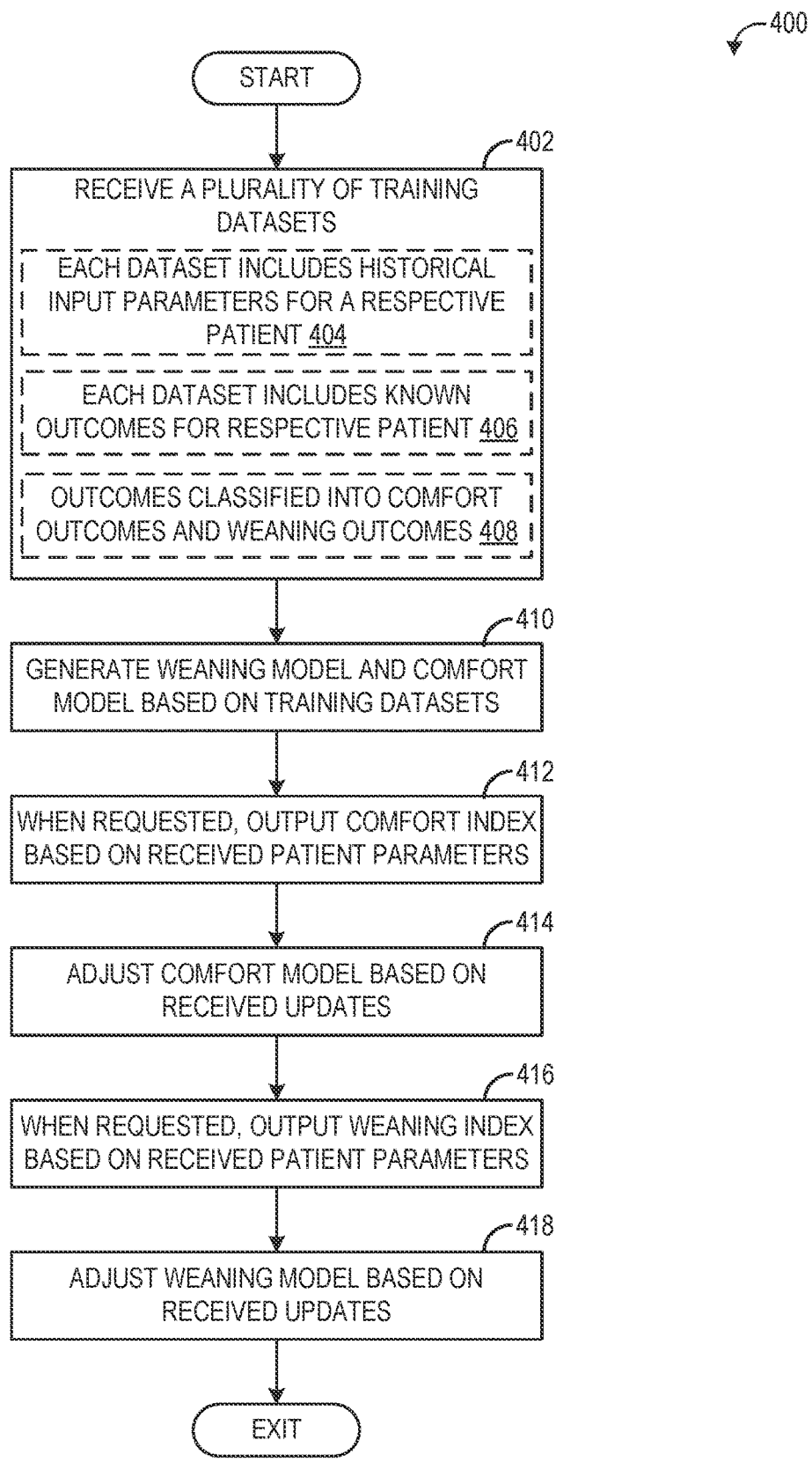
FIG. 4 is a flow chart illustrating a method for training and executing a weaning assistant.

FIG. 4 is a flow chart illustrating a method 400 for training and executing a weaning assistant, such as weaning assistant 126 of FIG. 1. Method 400 may be executed by a processor of a computing device according to instructions stored on a non-transitory memory of the device (such as processor(s) 124 and memory 122 shown in FIG. 1 or processor(s) and memory of a device in communication with controller 102 of FIG. 1, such as a central server). At 402, a plurality of training datasets are received. Each training dataset may include historical input parameters for a respective patient that was previously housed in a microenvironment, as indicated at 404. A suitable number of training datasets may be received, such as 200 or 500 datasets. The historical input parameters may include measured/monitored medical parameters, including but not limited to patient respiration rate, heart rate, temperature, body weight, sucking reflex, date of birth relative to due date, total duration of stay in a microenvironment, days since birth, microenvironment conditions during the patient's stay in the microenvironment (e.g., air temperature and humidity), and ambient conditions at the time of patient weaning (e.g., ambient temperature, humidity, and particulate matter level). At least some of the parameters may include more than one data point. For example, a plurality of patient respiration rates may be received, each respiration rate measured at a different point in time over the course of the respective patient's stay in the microenvironment. In examples where more than one data point of a given parameter is received for a patient, each data point may be tagged with the time/day that the parameter was measured. In some examples, the patient parameters may include ambient conditions in the environment in which the patient resided upon being discharged from the microenvironment/medical facility. For example, the ambient conditions may include air humidity, air particulate matter level, air temperature, etc., of the patient environment. In some examples, the ambient conditions may be approximated/inferred based on patient location.

Each training dataset may further include known outcomes for each respective patient, as indicated at 406. For example, the known outcomes may include outcomes measured while the patient was still in the microenvironment (e.g., duration of time in microenvironment, trajectory of parameters during the time in the microenvironment) as well as outcomes measured after the patient was weaned from the microenvironment (e.g., duration of patient stay in the microenvironment before being weaned, how long after being weaned was the patient discharged from the medical facility, whether the patient was readmitted to the microenvironment, whether the patient was readmitted to the medical facility for a complication related to the initial placement in the microenvironment, and/or any other complications).

In some examples, the known outcomes may be classified into comfort outcomes and weaning outcomes, as indicated at 408. As explained above, the weaning assistant may be trained to calculate both a comfort index and a weaning index. The weaning index may be used by a clinician to determine whether a patient is stable/developed/healthy enough to be weaned from a microenvironment. The comfort index may be used by the microenvironment controller to determine whether the patient is ready to start or continue the gradual microenvironment temperature reduction of the weaning protocol described above with respect to FIG. 3. Accordingly, the weaning assistant may be trained using different outcomes (or different sets of outcomes) in order to be able to determine a weaning index and a comfort index. As one example, the outcome(s) classified into the comfort outcomes may include patient status/trajectory during the patient's stay in the microenvironment (e.g., whether the patient's parameters steadily improved toward weaning or whether the patient's parameters declined or otherwise failed to steadily improve over the course of the patient's stay in the microenvironment, whether the patient was able to be weaned in a reasonable time frame, whether the patient was able to maintain a stable body temperature as microenvironment temperature changed, and/or whether the patient developed any complications while in the microenvironment), while outcomes classified into the weaning outcomes may include the known outcomes once the patient was weaned from the microenvironment (e.g., how long after being weaned was the patient discharged from the medical facility, whether the patient was readmitted to the microenvironment, any complications, etc.).

Figure 7:
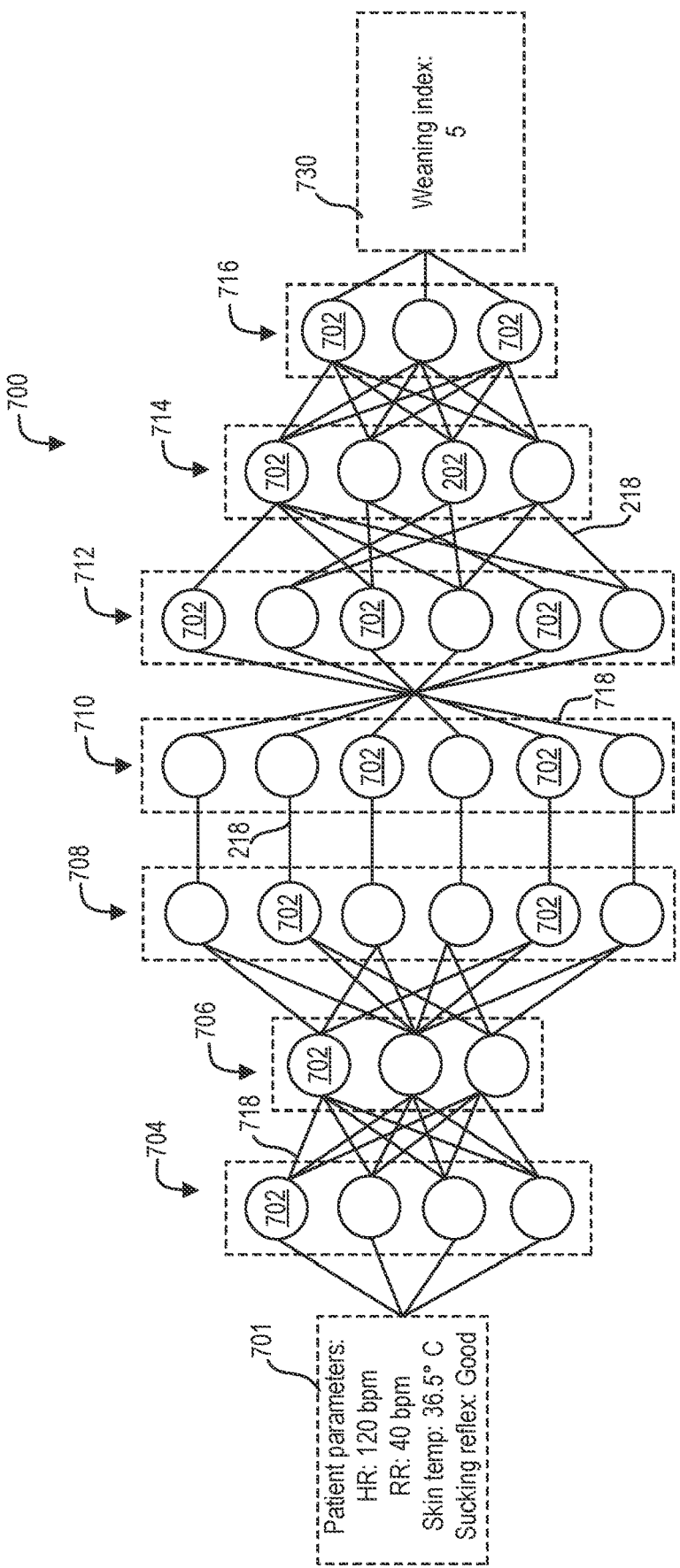
FIG. 7 shows a schematic diagram illustrating an example neural network.

At 410, a weaning model and a comfort model are generated based on the training datasets. The weaning model and comfort model may take any suitable form depending on the method of machine learning being performed. For example, if the weaning assistant is trained using a random forest learning algorithm, the weaning model and comfort model may each include decision trees. In another example, if the weaning assistant is trained using artificial neural networks, the weaning model and comfort model may each include layers of connected artificial neurons (as shown in FIG. 7 and explained in more detail below). The weaning model may be configured to output a weaning index (e.g., which may be a number on a scale of 1-5) when a plurality of patient parameters (such as current respiration rate, heart rate, temperature, and sucking reflex) are entered as inputs to the weaning model. The comfort model may be configured to output a comfort index when a plurality of current patient parameters (which may be the same parameters as entered into the weaning model) are entered as inputs to the comfort model.

At 412, the comfort model outputs a comfort index based on received patient parameters, when requested by a user or another computing device in communication with the weaning assistant. For example, a comfort index may be requested by controller 102 during execution of method 200 of FIG. 2 and/or during execution of method 300 of FIG. 3. The weaning assistant may receive the current patient parameters from controller 102 (and/or other source(s), such as monitoring devices 108) and enter the current patient parameters as inputs to the comfort model. The weaning assistant may then send the output from the comfort model (e.g., the comfort index) to controller 102.

At 414, the comfort model is adjusted based on received updates. As explained above with respect to FIG. 2, a comfort index may be obtained for a given patient when the patient's temperature has been at a set patient temperature for a duration, and if the comfort index indicates that the patient is ready for a weaning protocol to be initiated (e.g., the comfort index is above a threshold), the weaning protocol may be initiated to gradually lower the microenvironment air temperature. Prior to commencing the weaning protocol, user input may be obtained to confirm that a clinician overseeing care of the patient agrees that the patient is ready to undergo the weaning protocol. If user confirmation is not received, for example if the user enters an input indicating that the patient should not undergo the weaning protocol, and update may be sent to the weaning assistant notifying the weaning assistant that the weaning protocol was not initiated. The weaning assistant may learn from the update by making changes to the comfort model. For example, the significance of the current patient parameters used to obtain the comfort index may be lowered in the comfort model.

At 416, the weaning model outputs a weaning index based on received patient parameters, when requested by a user or another computing device in communication with the weaning assistant. For example, a weaning index may be requested by controller 102 during execution of method 300 of FIG. 3. The weaning assistant may receive the current patient parameters from controller 102 (and/or other source(s), such as monitoring devices 108) and enter the current patient parameters as inputs to the weaning model. The weaning assistant may then send the output from the weaning model (e.g., the weaning index) to controller 102. The patient parameters input to the weaning model include current patient parameters (e.g., respiration rate, heart rate, temperature, sucking reflex). In some examples, the input to the weaning model may additionally include anticipated ambient conditions in the future patient environment if the patient is weaned, such as anticipated air humidity and particulate matter level in the home in which the patient will reside once discharged from the medical facility. In this way, the impact that the environment may have on the patient, and the patient likelihood of successfully residing outside the microenvironment, may be taken into account. The anticipated ambient conditions may be obtained from a remote service, such as a weather service, based on the patient's home location and/or entered by a user.

At 418, the weaning model is adjusted based on received updates. As explained above with respect to FIG. 3, a weaning index may be obtained for a given patient when requested by a clinician and/or when the patient's comfort index has remained above a threshold while the microenvironment air temperature is lowered to ambient temperature. If the user/clinician commences weaning upon receiving the weaning index, an update may be sent to the weaning assistant notifying the weaning assistant that the patient was weaned. Likewise, if the clinician chooses not to wean the patient, an update may be sent to the weaning assistant notifying the weaning assistant that the patient was not weaned The weaning assistant may learn from the update by making changes to the weaning model. For example, the significance of the current patient parameters used to obtain the weaning index may be lowered in the weaning model, if the patient is not weaned. Other updates for the weaning model that may be sent to the weaning assistant include subsequent patient outcomes, such as whether the patient was readmitted to the microenvironment upon being weaned from the microenvironment, actual ambient conditions in the patient's environment following weaning (e.g., measured air humidity, temperature, and particulate matter level), weight gain following weaning, and/or complications following weaning. The subsequent outcomes may be sent to the weaning assistant from a medical record database, such as EGR database 116 of FIG. 1. To ensure the subsequent outcomes are associated with the correct patient (since the subsequent outcomes may be sent in the days, weeks, or even months following the calculation of the weaning index for the patient), each time a comfort index and/or weaning index is calculated for a patient, the patient parameters for that patient may be tagged with a patient ID number or other identifier, the comfort index and/or weaning index for that patient may be tagged with the identifier, and the subsequent outcomes may be tagged with the identifier. Method 400 then ends.

FIGS. 5 and 6 show example timelines for a patient housed in a microenvironment, such as microenvironment 104 of FIG. 1. The timelines may include measured microenvironment and patient parameters as well as the obtained comfort index and weaning index for the patient during the execution of the methods of FIGS. 2 and 3, for example. FIG. 5 shows a first timeline 500 for the patient. Timeline 500 includes a microenvironment air temperature plot 502, a patient temperature plot 504, a comfort index plot 506, and a weaning index plot 508. Each parameter is plotted as a function of time (shown on the x-axis), and each parameter is time-aligned. Microenvironment air temperature and patient temperature are each in ° C. with relative values shown on the y-axis. The comfort index and weaning index are each on a scale of 1-5, shown on the y-axis.

Prior to time t1, the microenvironment air temperature is controlled by controlling a heating device of the microenvironment according to a feedback control scheme, and is at a constant temperature of 30° C. The patient temperature is approximately 36.5° C., which is in range of a set patient temperature. At time t1, the patient temperature has been in range of the set patient temperature for at least 24 hours, and thus a comfort index for the patient is obtained. The first comfort index (obtained at time t1) is above a comfort index threshold 510. Thus, a user of the system (such as a clinician) enters a confirmation that the weaning protocol should be initiated, which causes the heating device to be controlled in a weaning mode, where the controller gradually adjusts the microenvironment air temperature. At time t2, the microenvironment air temperature is lowered by a degree, and after a suitable amount of time (e.g., an hour), a second comfort index for the patient is obtained just before time t3. The second comfort index is above the threshold, so the microenvironment air temperature is lowered by another degree at time t3. Just before t4, which may be an hour after t3, a third comfort index for the patient is obtained, which is still above the threshold, so the microenvironment air temperature is lowered by another degree at time t4.

Just before t5, which may be an hour after t4, a fourth comfort index for the patient is obtained However, potentially due to the decrease in the patient temperature that occurred between t2-t5, the fourth comfort index is below the threshold. As a result, the weaning protocol is stopped and the heating device of the microenvironment is switched back to the feedback mode, where after the microenvironment is preheated (in the illustrated example, the microenvironment air temperature is controlled to a temperature above ambient, herein 30° C.), the microenvironment air temperature is controlled based on the patient temperature. The weaning index for the patient is obtained and displayed to the user at time t5. The weaning index has a value of 3, and thus the medical facility guidelines may dictate that the patient be re-evaluated for weaning in a specified duration, such as 24 or 48 hours.

FIG. 6 shows a second timeline 600 for the patient. Timeline 600 includes a microenvironment air temperature plot 602, a patient temperature plot 604, a comfort index plot 606, and a weaning index plot 608. Each parameter is plotted as a function of time (shown on the x-axis), and each parameter is time-aligned. Microenvironment air temperature and patient temperature are each in ° C. with relative values shown on the y-axis. The comfort index and weaning index are each on a scale of 1-5, shown on the y-axis. Timeline 600 may commence after the specified duration, such as 24 or 48 hours after the weaning protocol was stopped in the timeline 500 of FIG. 5.

Prior to time t1 of timeline 600, the microenvironment air temperature is controlled by controlling a heating device of the microenvironment according to a feedback control scheme, and is at a constant temperature of 30° C. The patient temperature is approximately 36.5° C., which is in range of a set patient temperature. At time t1, the patient temperature has been in range of the set patient temperature for at least 24 hours, and thus a comfort index for the patient is obtained. The first comfort index (obtained at time t1) is above a comfort index threshold 610. Thus, a user of the system (such as a clinician) enters a confirmation that the weaning protocol should be initiated, which causes the heating device to be controlled in a weaning mode, where the controller gradually adjusts the microenvironment air temperature. At time t2, the microenvironment air temperature is lowered by a degree, and after a suitable amount of time (e.g., an hour), a second comfort index for the patient is obtained just before time t3. The second comfort index is above the threshold, so the microenvironment air temperature is lowered by another degree at time t3. Just before t4, which may be an hour after t3, a third comfort index for the patient is obtained, which is still above the threshold, so the microenvironment air temperature is lowered by another degree at time t4.

Just before t5, which may be an hour after t4, a fourth comfort index for the patient is obtained, which is still above the threshold, so the microenvironment air temperature is lowered by another degree at time t5. The process is repeated at times t6, t7, and t8 (e.g., the comfort index is obtained, and because the comfort index is above the threshold, the temperature is lowered by another degree). After lowering the temperature at time t8, the microenvironment temperature is at ambient temperature. After a period of time has elapsed while at ambient temperature, the weaning index for the patient is obtained and displayed to the user at time t9. The weaning index has a value of 5, thus indicating the patient has a high likelihood of being successfully weaned. If desired, the clinician may then remove the patient from the microenvironment.

As explained above, the weaning index and/or comfort index may be determined with an AI-based module, such as weaning assistant 126, using a suitable machine learning algorithm. As an illustrative example, FIG. 7 depicts a neural network 700 having one or more nodes/neurons 702 which, in some embodiments, may be disposed into one or more layers 704, 706, 708, 710, 712, 714, and 716. The neural network 700 may be a deep neural network. As used herein with respect to neurons, the term "layer" refers to a collection of simulated neurons that have inputs and/or outputs connected in similar fashion to other collections of simulated neurons. Accordingly, as shown in FIG. 7, the neurons 702 may be connected to each other via one or more connections 718 such that data may propagate from an input layer 704, through one or more intermediate layers 706, 708, 710, 712, 714 to an output layer 716.

Figure 8:
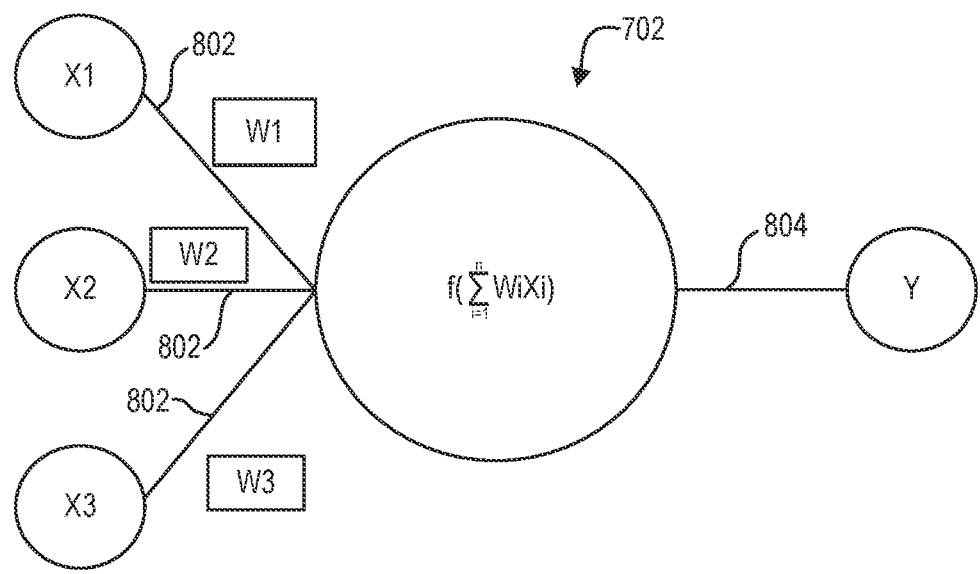
FIG. 8 shows a schematic diagram illustrating an example node of a neural network.

FIG. 8 shows input and output connections for a neuron in accordance with an exemplary embodiment. As shown in FIG. 8, the connections 718 of an individual neuron 702 may include one or more input connections 802 and one or more output connections 804. Each input connection 802 of a neuron 702 may be an output connection of a preceding neuron, and the output connections 804 of the neuron 702 may be an input connection of one or more subsequent neurons. While FIG. 8 depicts a neuron 702 as having a single output connection 804, it should be understood that neurons may have multiple output connections that transmit/pass the same value. In embodiment, the neurons 702 may be data constructs, e.g., structures, instantiated class objects, matrices, etc., and the input connections 718 may be received by the neuron 702 as weighted numerical values, e.g., floating point or integer values. For example, as further shown in FIG. 8, input connections X1, X2, and X3 may be weighted via weights W1, W2, and W3, respectively, summed, and sent/transmitted/passed as output connection Y. As will be appreciated, the processing of an individual neuron 702 may be represented, generally, by the equation:

$$Y = f(\sum_{i=1}^{n} WiXi)$$

where n is the total number of input connections 802 to the neuron 702. In embodiment, the value of Y may be based at least in part on whether the summation of WiXi exceeds a threshold. For example, Y may have a value of zero (0) if the summation of the weighted inputs fails to exceed a desired threshold.

As will be further understood, the input connections 802 of neurons 702 in the input layer 704 may be mapped to the input 701, while the output connections 804 of the neurons 702 in the output layer 716 may be mapped to the output 730. As used herein, "mapping" an input connection 802 to the input 701 refers to the manner by which the input 701 affects/dictates the value of the input connections 802. Similarly, as also used herein, "mapping" an output connection 804 to the output 730 refers to the manner by which the value of the output connections 804 affects the output 730.

Accordingly, in embodiments, the acquired/obtained input 701 is passed/fed to the input layer 704 of the neural network 700 and propagated through the layers 704, 706, 708, 710, 712, 714, and 716 such that mapped output connections 804 of the output layer 716 generates/corresponds to the output 730. As shown, the input 701 includes measured/obtained patient parameters for a patient currently housed in a microenvironment, such as the patient discussed above with respect to FIGS. 5 and 6, where the patient parameters include heart rate, respiration rate, skin temperature, and sucking reflex. The output 730 includes the weaning index, in the case a weaning index having a value of 5.

The deep neural network 700 may be trained using a plurality of training datasets. Each training dataset may include a plurality of patient parameters for a respective prior patient and one or more known outcomes for the respective prior patient, where each respective prior patient was previously housed in a thermoregulated microenvironment (and subsequently weaned from the microenvironment). For each prior patient, the plurality of patient parameters may be obtained prior to the respective prior patient being weaned from the thermoregulated microenvironment (e.g., in the case of patient vital signs) and/or after the respective prior patient was weaned from the microenvironment (e.g., in the case of ambient environmental parameters, such as air humidity and particulate matter level in the patient's home). Further, for each prior patient, the one or more known outcomes may include patient status after being weaned from the thermoregulated microenvironment. The known outcomes may be quantified (e.g., a patient that was not readmitted to the microenvironment or medical facility and did not develop complications may have an outcome that is quantified as a 5, while a patient that was readmitted to the microenvironment within 24 hours of being weaned may be given a known outcome that is quantified as a 4). In this way, the inputs to the neural network (e.g., the patient parameters) may be mapped to the known outcomes, and the known outcomes may be quantified via the weaning index (and/or comfort index). Further, as explained previously, the weaning model (e.g., neural network) may continue to learn and update as additional inputs and updates are received. For example, if a patient is assigned a weaning index of 4 but is not weaned, the weaning assistant may receive an update that the patient was not weaned despite the high weaning index. The learning (such as in response to the lack of weaning) may cause the weights (e.g., W1, W2, and/or W3) to change, the input/output connections to change, or other adjustment to the neural network.

The technical effect of calculating a weaning index using an artificial intelligence based weaning assistant module is that a clinician may opt to wean a patient housed in a microenvironment off the microenvironment when the patient's medical/health parameters indicate the patient has a higher likelihood for being successfully weaned, as predicted by the weaning index. By utilizing the weaning index, and possibly instituting a gradual and automatically controlled decrease in microenvironment temperature (and/or other environmental parameters such as humidity) before removing the patient from the microenvironment, adverse patient outcomes stemming from patients being weaned too early may be avoided.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:
   obtaining a plurality of current patient parameters of the patient in response to a request to calculate a weaning index for a patient housed in a thermoregulated environment;
   sending the plurality of current patient parameters to a weaning assistant configured to calculate the weaning index based on the plurality of current patient parameters and historical data for a plurality of prior patients previously housed in a thermoregulated microenvironment;
   receiving the weaning index from the weaning assistant;
   displaying the weaning index on a display device;
   upon displaying the weaning index, receiving one or more subsequent patient outcomes, the one or more subsequent patient outcomes including whether the patient was readmitted to the microenvironment within a duration since being weaned from the microenvironment, whether the patient developed any complications within the duration since being weaned from the microenvironment, or ambient conditions when the patient was weaned from the microenvironment; and
providing the one or more subsequent patient outcomes to the weaning assistant for updating a weaning model based on the one or more received subsequent patient outcomes,
wherein the request to calculate the weaning index is generated upon completion of a weaning protocol, and wherein the weaning protocol gradually reduces a temperature of the microenvironment until the temperature reaches ambient temperature.

2. The method of claim 1, wherein upon displaying the weaning index, the method further comprises receiving an indication of patient weaning status and sending a notification of the patient weaning status to the weaning assistant.

3. The method of claim 2, wherein receiving the indication of the patient weaning status comprises receiving a first indication that the patient is currently being weaned or a second indication that the patient is not currently being weaned, the first indication or second indication received via user input and/or via signals output from the microenvironment, the notification usable by the weaning assistant to update future weaning index calculations.

4. The method of claim 1, further comprising upon displaying the weaning index, sending one or more notifications of subsequent patient outcomes to the weaning assistant, the one or more notifications usable by the weaning assistant to update future weaning index calculations.

5. The method of claim 1, wherein the plurality of current patient parameters comprises a first plurality of current patient parameters, and further comprising performing the weaning protocol by:
obtaining a first comfort index of the patient by obtaining a second plurality of current patient parameters while the thermoregulated microenvironment is at the reduced temperature and sending the second plurality of current patient parameters to the weaning assistant, the weaning assistant configured to calculate the first comfort index for the patient based on the second plurality of current patient parameters and the historical data;
responsive to the first comfort index being above a threshold, iteratively reducing the temperature of the thermoregulated microenvironment and obtaining an additional comfort index each time the temperature of the thermoregulated microenvironment is reduced; and
once the temperature of the thermoregulated microenvironment is at the ambient temperature, generating the request to calculate the weaning index.

6. The method of claim 5, wherein the first plurality of current patient parameters comprise a respiration rate of the patient, a heart rate of the patient, a temperature of the patient, a gestational age of the patient, a number of days since birth of the patient, and/or an oral sucking reflex of the patient each obtained at a first point in time.

7. The method of claim 6, wherein the second plurality of current patient parameters comprise the respiration rate of the patient, the heart rate of the patient, the temperature of the patient, the gestational age of the patient, the number of days since birth of the patient, and/or the oral sucking reflex of the patient each obtained at a second point in time earlier than the first point in time.

8. The method of claim 1, wherein the historical data comprises a plurality of training datasets, each training dataset comprising patient parameters for a respective prior patient and one or more known outcomes for the respective prior patient, the patient parameters including a respiration rate of the respective prior patient, a heart rate of the respective prior patient, a temperature of the respective prior patient, a gestational age of the respective prior patient when weaned, a number of days after birth of the respective prior patient when weaned, an oral sucking reflex of the respective prior patient, and ambient conditions during or after weaning.

* * * * *